(12) United States Patent
O'Connell et al.

(10) Patent No.: US 7,342,228 B1
(45) Date of Patent: Mar. 11, 2008

(54) METHOD AND APPARATUS FOR MEASUREMENT OF AEROSOLS AND IMAGING

(75) Inventors: Daniel G. O'Connell, Kihei, HI (US);
S. Maile Giffin, Kihei, HI (US);
Christopher J. Sullivan, Honolulu, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 211 days.

(21) Appl. No.: 10/654,006

(22) Filed: Sep. 4, 2003

Related U.S. Application Data

(60) Provisional application No. 60/408,270, filed on Sep. 6, 2002.

(51) Int. Cl.
*G01N 21/35* (2006.01)
(52) U.S. Cl. .................................... 250/339.06
(58) Field of Classification Search ........... 250/370.08, 250/458.1, 459.1, 341.1, 338.1, 338.5, 339.01, 250/339.06, 339.07; 356/341, 601
See application file for complete search history.

(56) References Cited

U.S. PATENT DOCUMENTS

| | | | | |
|---|---|---|---|---|
| 6,031,850 | A * | 2/2000 | Cheo | 372/6 |
| 6,081,369 | A * | 6/2000 | Waarts et al. | 359/341.33 |
| 6,246,468 | B1 * | 6/2001 | Dimsdale | 356/4.02 |
| 6,448,572 | B1 * | 9/2002 | Tennant et al. | 250/559.38 |
| 6,518,562 | B1 * | 2/2003 | Cooper et al. | 250/222.2 |
| 6,542,227 | B2 * | 4/2003 | Jamieson et al. | 356/28.5 |
| 6,593,582 | B2 * | 7/2003 | Lee et al. | 250/458.1 |
| 6,608,669 | B2 * | 8/2003 | Holton | 356/28.5 |
| 6,664,533 | B1 * | 12/2003 | van der Laan et al. | 250/222.2 |
| 6,847,462 | B1 * | 1/2005 | Kacyra et al. | 356/601 |

OTHER PUBLICATIONS

Kolev, I.; Parvanov, O.; and Kaprielov, B; *Lider determination of winds by aerosol inhomogeneities—Motion velocity in the planetary boundary layer*; Applied Optics; vol. 27, Jun. 15, 1988; pp. 2524-2531; (Abstract only).

Taczak, T.M. and Killinger, D.K.; *Development of a tunable, narrow-linewidth, cw 2,0676-μm Ho:YFL laser for remote sensing of atmospheric $CO_2$ and $H_2O$*; Applied Optics; vol. 37, No. 26, Dec. 20, 1988; pp. 8460-8476.

Paschotta, R. et al.; *Passively Q-switched 0.1-mJ fiber laser system at 1.53 μm*; Optics Letters; vol. 24, No. 6; Mar. 15, 1999; pp. 388-390.

* cited by examiner

*Primary Examiner*—Constantine Hannaher
(74) *Attorney, Agent, or Firm*—James Creighton Wray; Clifford D. Hyra

(57) ABSTRACT

A lightweight, low-cost, and highly sensitive aerosol sensor measures aerosol concentrations remotely. A fiber laser sends pulses outward toward the target area from a carbon-fiber telescope using ultra-lightweight optical elements. Light is received back in the same telescope or in another similar telescope depending on the aerosol concentration or other contents of the atmosphere. The sensor is lightweight, low-cost and has high performance. The system also measures aerosol profiles over a hemispherical volume to produce a three-dimensional measurement within the range of the laser.

50 Claims, 5 Drawing Sheets

METHOD AND APPARATUS FOR MEASUREMENT OF AEROSOLS AND IMAGING

This application claims the benefit of U.S. Provisional Application No. 60/408,270 filed Sep. 6, 2002.

BACKGROUND OF THE INVENTION

Light Detection And Ranging (lidar) is a method of measuring concentrations of various constituents in the atmosphere. In this method radiation in the form of light is emitted from a source and is scattered when it reaches certain molecules. Some of the scattered light returns toward a light-sensing device, indicating both the concentration of certain molecules and the distance to the measurement.

Conventional lidar aerosol detection systems are either too expensive or lack the sensitivity to sufficiently determine atmospheric aerosol gradients. There is a need for a compact, low-cost, sensitive aerosol-detecting lidar system for air quality assessment, prediction and management.

SUMMARY OF THE INVENTION

The present scanning aerosol detector is useful in a wide variety of applications, including cloud ceiling measurements. The device is retrofitted for additionally functioning as a scanning ceilometer. The invention's applications include use aboard United States Navy ships as both a cloud height measurement tool and as a warning device to detect the use of Chemical and Biological Warfare agents dispersed in aerosol form.

The invention is an inexpensive lightweight detector device which may be mounted on buildings to allow forewarning of impending abnormal airborne pollution events that might pose as health hazards. Additionally, the device when mounted on a vehicle allows temporary measurement stations to be set up in regions of particular interest to scientists which may include, for example, earthquake fault lines or areas of volcanic eruptions.

The demand for a low-cost, high-sensitivity aerosol lidar comes from various segments of the community. First, metropolitan areas where air pollution is a problem can install a series of these units in the area to monitor atmospheric conditions, which aggravate or alleviate air pollution. Air pollution is a problem around the world.

The present instruments can also be deployed by weather agencies for more comprehensive monitoring of atmospheric conditions and for improving weather modeling and prediction. Furthermore, demand exists for use of this technology to improve cloud ceiling height measurement at airports and provide sector visibility measurements. A dual-use version can be of great use to weather service and air traffic control agencies.

An all solid-state laser system has the advantages of simplicity, compactness, stability and energy-efficiency. However, these systems still fall short in either the cost or performance stakes. Diode-based laser systems are popular because they are relatively small, simple, robust, very energy-efficient (~40% QE), and inexpensive to produce in large quantities. Diode lasers are available on many different wavelengths, but mostly fall between 800-980 nm wavelengths. Therefore, eye safety must be achieved by expanding the transmitted laser beam, reducing the peak power density. Although diode lasers are rugged, the limited energy per pulse delivered by these systems reduces the sensitivity required for aerosol detection.

Another route for lidar systems is to use rare earth or transition metal lasers with various dopants for tunable high power laser output. Although these systems achieve excellent operating specifications for cloud and aerosol detection, they are also very expensive systems and are much less robust than diode lasers.

Since the advent of optical communications and silica based fiber optics, the development of fibers that can operate at lower loss and higher power has significantly advanced. Erbium doped and erbium-ytterbium co-doped materials are arriving at the forefront of high-power fiber lasers.

These and further and other objects and features of the invention are apparent in the disclosure, which includes the above and ongoing written specification, with the claims and the drawings.

BRIEF DESCRIPTION OF THE DRAWINGS

FIG. 1: Schematic diagram of fiber ring laser
  1. Erbium doped fiber amplifier
  2. Angled connection
  3. Optical isolator
  4. Acousto-optic modulator with driver
  5. Fiber splice
  6. Output coupler
  7. Laser emission
  8. Pulse generator
  9. Fiber
  10. Fiber ring laser
FIG. 2: Basic receiver telescope design.
  7. Laser emission (from FIG. 1)
  11. Plano-concave lens
  12. Plano-convex lens
  13. Beam steering mirror
  14. Telescope tube
  15. Secondary mirror
  16. Computer
  17. Cables
  18. Digital oscilloscope
  19. Amplifier
  20. Avalanche photodiode
  21. Filter
  22. Beam splitter
  23. Lens
  24. Primary mirror
  25. Detector
FIG. 3: Afocal beam expander configuration.
  26. Lightweight carbon fiber tube
  27. Lightweight primary mirror
  28. Secondary mirror mounted to interchangeable spider ring
  29. Collimated input beam
FIG. 4: Telescope in Cassegrain configuration
  26. Lightweight carbon fiber tube
  27. Lightweight primary mirror
  28. Secondary mirror mounted to interchangeable spider ring
  30. Cassegrain focus
FIG. 5: Dual Lidar/Imaging mode configuration
  26. Lightweight carbon fiber tube 27. Lightweight primary mirror
28. Secondary mirror mounted to interchangeable spider ring
31. Dichroic beam splitter
32. Reimaging lens
33. Imaging camera
34. Laser interface

DETAILED DESCRIPTION OF PREFERRED EMBODIMENTS

The present system is a fiber based laser system, operating in the eye-safe regime, that rapidly collects 3D cloud information as well as detects aerosols. Fiber lasers are robust enough for use in the field, and their specifications are significantly more flexible than solid-state crystal lasers. A fiber laser has some of the same advantages of a diode laser, in that it can be made compact and fairly rugged. It also has the advantage of operating at the longer wavelength of 1.55 µm and can deliver significantly more energy per pulse than current extra-cavity diode lasers operating at this wavelength.

The system uses a moderately high power erbium (Er) fiber laser operating at 1.55 µm. This enables the production of a compact, sensitive, and low-cost system. To produce a more efficient laser source, the Er-doped fiber laser is co-doped with ytterbium (Yb). The Yb is used as the "sensitizing" ion that strongly absorbs in a band that is not available to the laser ion. The pump energy is then transferred non-radiatively from $Yb^3$-ions to $Er^3$-ions, which emit around 1.55 µm wavelength.

The present lidar transceiver design uses an afocal telescope housed in a lightweight carbon fiber tube. Carbon fiber was chosen for several of its superior material properties such as a low coefficient of thermal expansion to maintain accurate optical spacings over a wide temperature range. The carbon fiber tube assembly also provides a stiffer structure than a metal housing of comparable wall thickness and can be made into a large tube, such that multiple telescope housings can be fabricated from the same carbon spin process and cut to length.

The optical design is a two-mirror afocal system that provides a convenient standardized input beam configuration, such that a collimated input beam is converted to a larger diameter collimated beam as it leaves the telescope. The telescope's secondary "spider ring" is a unique construction that is interchangeable with various secondary mirrors using the same primary mirror to cover a wide range of beam expansion ratios. This flexibility also allows the system to be configured in either an imaging mode (Cassegrain or Ritchey Chretien prescription) or as an afocal imaging system by using an interchangeable secondary ring.

Figure 1:
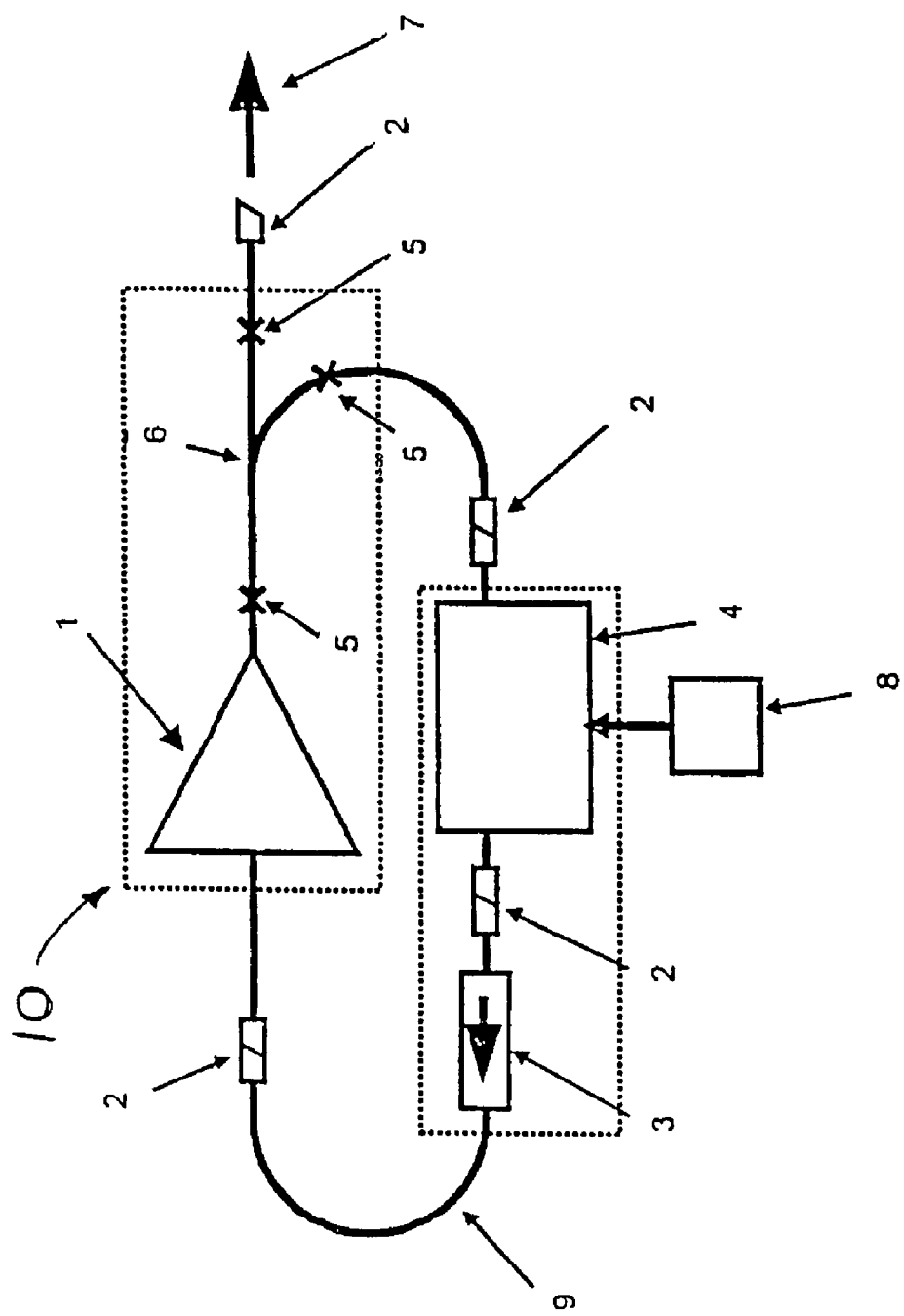
FIG. 1 shows a schematic diagram of a fiber ring laser.

FIG. 1 shows a schematic diagram of a fiber ring laser 10. Fiber ring laser 10 has an erbium doped fiber amplifier 1. Angled connections 2 connect the fibers between the parts. Optical isolator 3 is connected by an angled connector 2 to an acousto-optic modulator with driver 4. Fiber splices 5 connect output coupler 6 to amplifier 1, modulator 4 and an angled connector 2 for laser emission 7. Pulse generator 8 controls modulator 4. All elements are connected with fiber 9.

Figure 2:
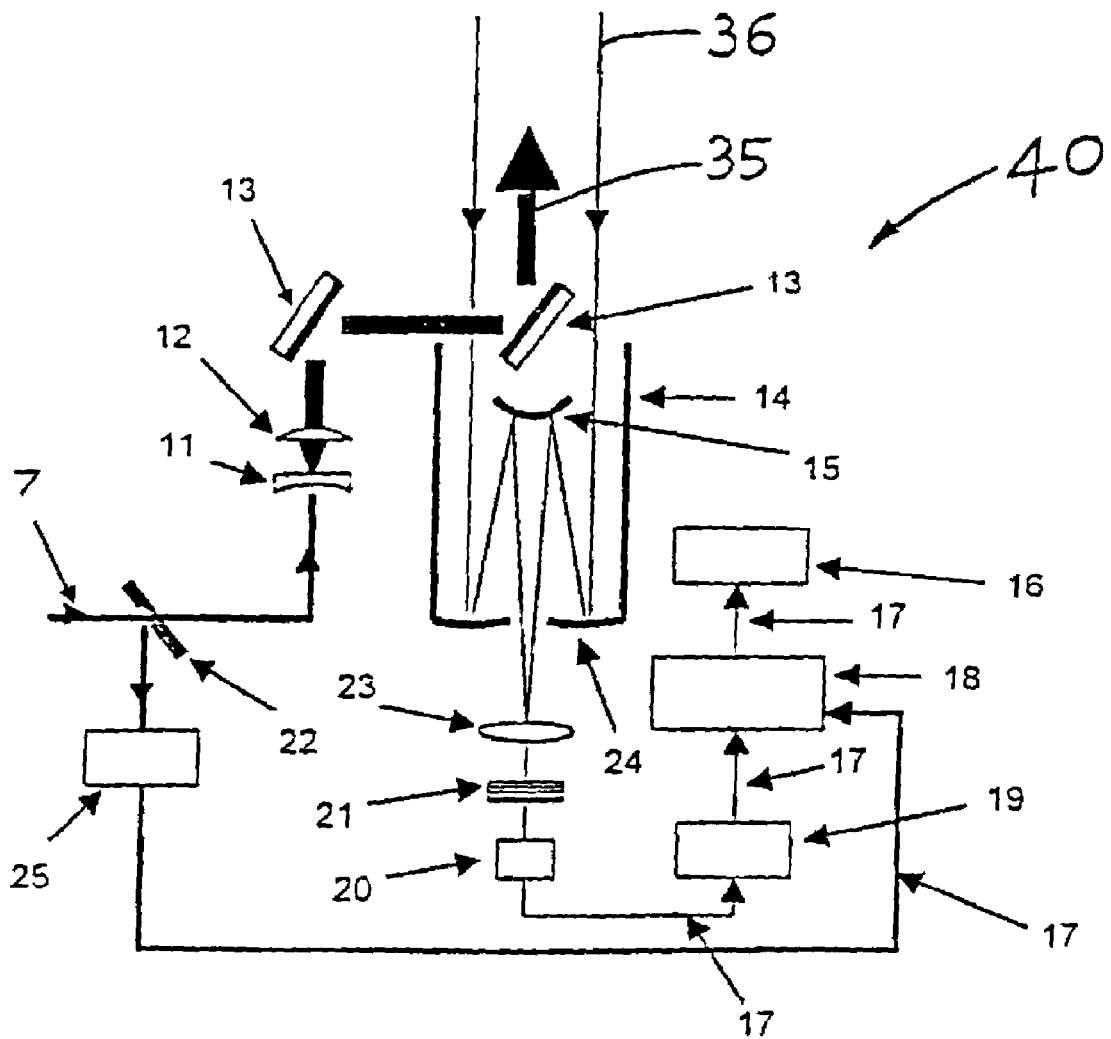
FIG. 2 shows a basic transceiver telescope.

FIG. 2 shows a basic transceiver telescope 40. The transceiver telescope 40 provides the laser emission 7 through a plano-concave lens 11 and a plano-convex lens 12. Beam steering mirrors 13 align laser output pulses 35 with telescope tube 14. Secondary mirror 15 provides return laser pulses 36 from a primary mirror 24 through lens 23 and filter 21 to avalanche photodiode array 20. A computer 16 and other elements are connected by cables 17 to a digital oscilloscope 18 and amplifier 19. Beam splitter 22 delivers part of laser emissions 7 to detector 25 as an input to oscilloscope 18.

Figure 6:
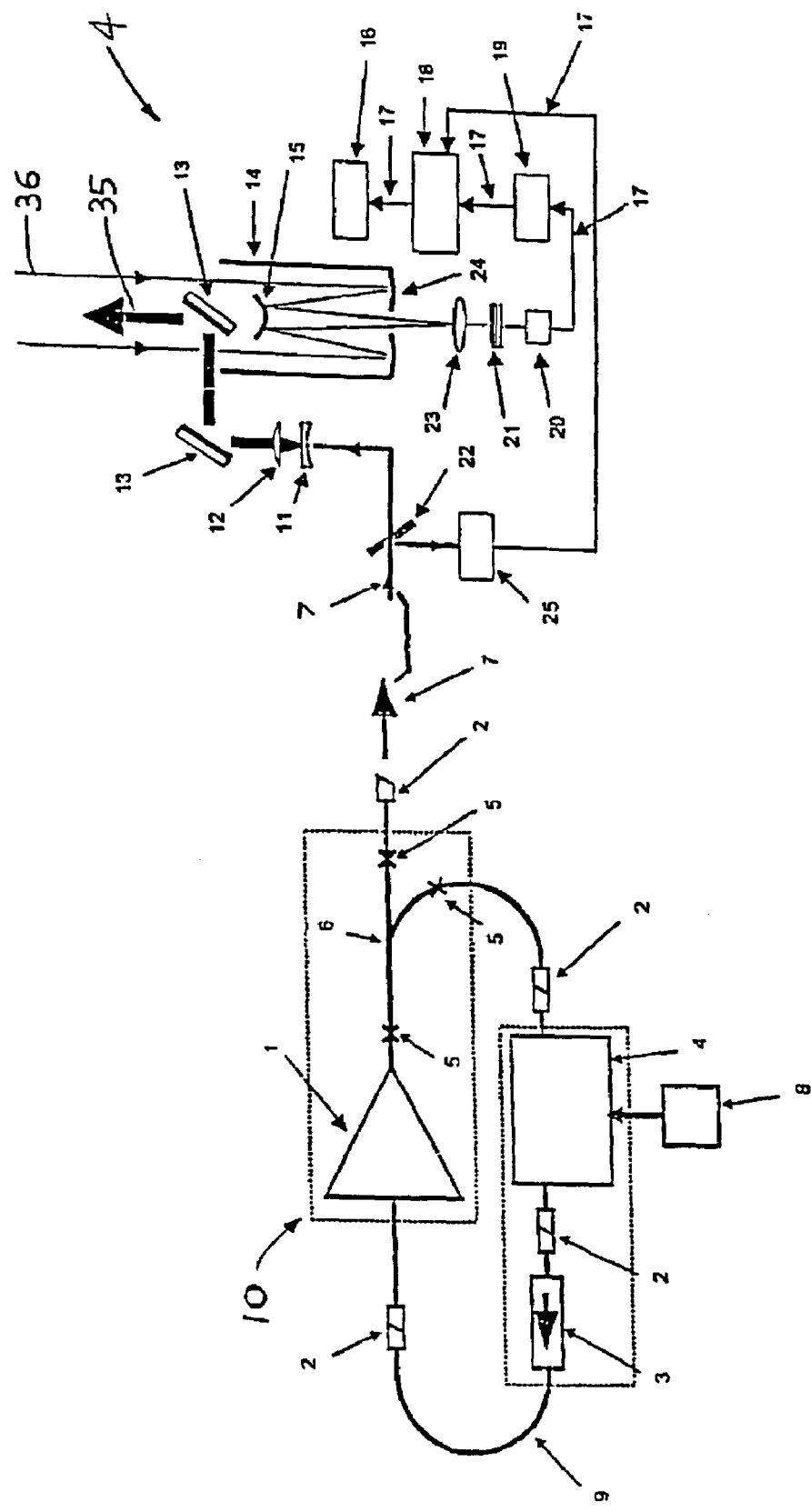
FIG. 6 shows a combined schematic view of the system shown in FIGS. 1 and 2.

FIG. 6 shows a combined schematic view of the system shown in FIGS. 1 and 2.

Figure 3:
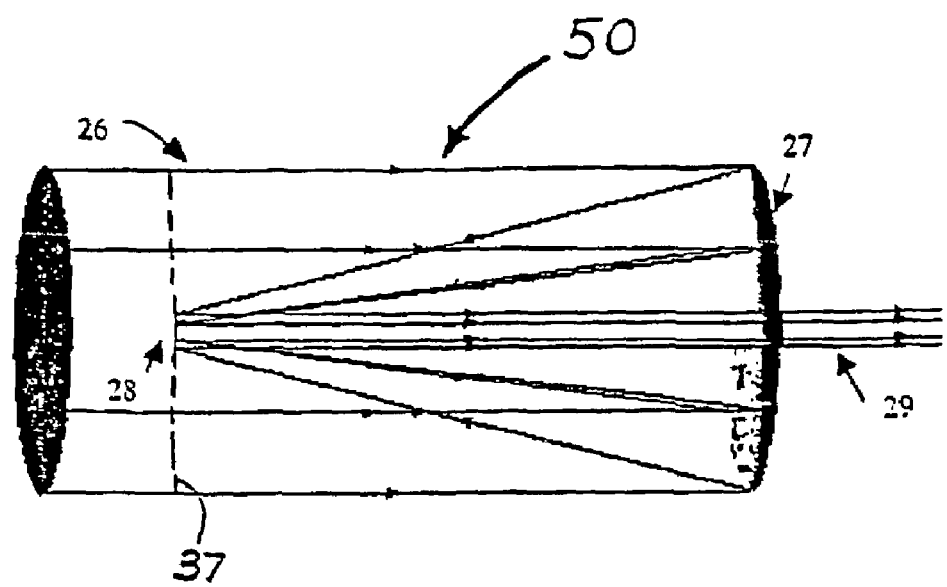
FIG. 3 shows an exemplary afocal beam expander.

FIG. 3 shows an exemplary afocal beam expander 50. Afocal beam expander 50 is mounted in a lightweight carbon fiber tube 26 with lightweight primary mirror 27. Secondary mirror 28 mounted on an interchangeable spider ring 37, provides a collimated input beam 29.

Figure 4:
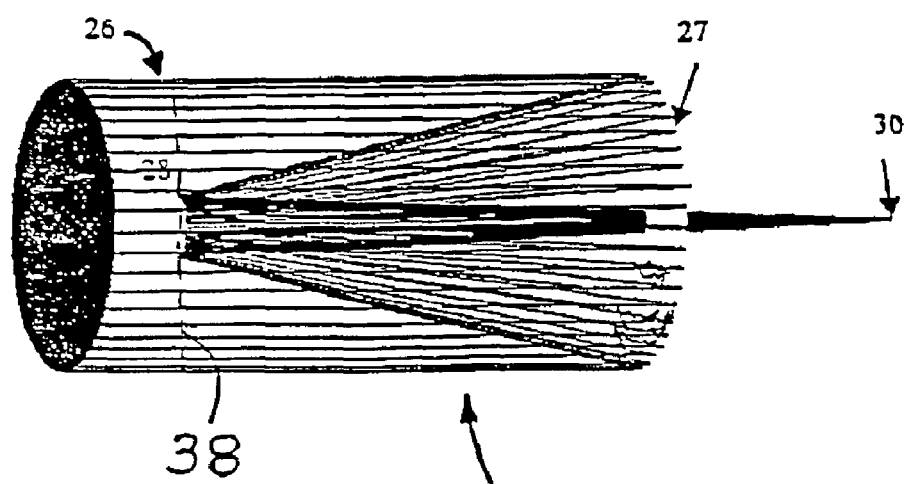
FIG. 4 shows an exemplary telescope used in Cassegrain configuration.

FIG. 4 shows an exemplary telescope 60 used in Cassegrain configuration. The telescope in Cassegrain configuration has a lightweight carbon fiber tube 26 with a lightweight primary mirror 27. A secondary mirror 28 mounted on an interchangeable spider ring 38, provides laser return in a Cassegrain focus 30.

Figure 5:
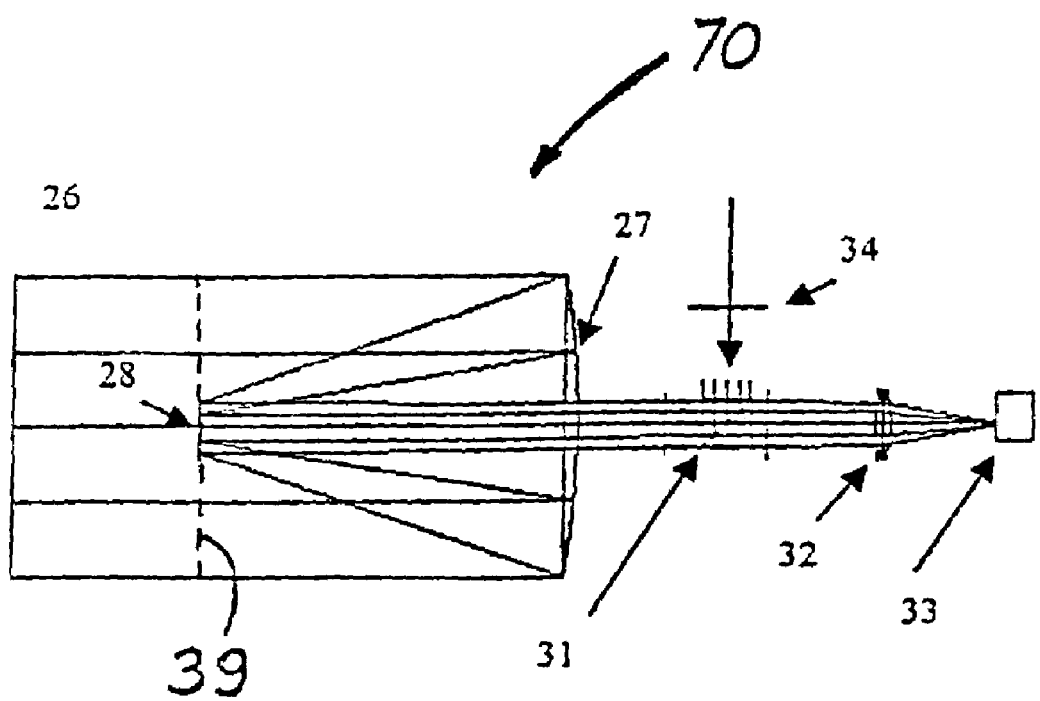
FIG. 5 shows an exemplary dual Lidar/Imaging mode configuration.

FIG. 5 shows an exemplary dual Lidar/Imaging mode configuration 70. The dual Lidar/Imaging mode configuration 70 has a lightweight carbon fiber tube 26 with a lightweight primary mirror 27. Secondary mirror 28 mounted on an interchangeable spider ring 39 provides return pulses through dichroic beam splitter 31 and reimaging lens 32 to imaging camera 33. Laser interface 34 provides images, such as, display images for direct viewing.

Preferably, the numerical aperture of the fiber laser is, but not limited to, NA=0.17, which produces a diverging beam with a focal ratio of F/2.94. The output of the fiber laser can be directly collimated with an F/2.94 lens producing a 1-inch diameter collimated beam, which serves as the input to the transceiver system. The 1-inch collimated beam enters the telescope where it is expanded up to, but not limited to, 5, 6, 7, or 8 inches. The telescope design is scalable for larger apertures as well, for use as desired. Alternatively, a low power lens can be used to reduce the divergence of the fiber laser to match the f/# of a telephoto type telescope configuration.

The mirrors of the telescope are preferably of lightweight material, such as but not limited to, borosilicate glass. The mirrors are fabricated by placing glass blocks in a kiln where they are heated until the glass flows into a preformed machined cast having a rib structure with open pockets. The resulting mirror is lighter and stiffer than conventional solid substrate mirrors. The mirrors may be of any kind, such as but not limited to spherical, aspherical, etc.

A dichroic beam splitter is located in between the fiber-laser collimator and telescope. This wavelength separating optical element reflects the laser wavelength towards the telescope secondary mirror. Light received by the telescope at visible wavelengths will pass through the beam splitter to an imaging camera that is aligned to a common optical axis. A re-imaging lens is mounted in front of the imaging camera, which combined with the telescope magnification results in a high magnification imaging system to view along the axis of the lidar transceiver.

This direct viewing provides the capability of infrared scene illumination and viewing for military or surveillance applications. This "invisible eye-safe flashlight" beam can illuminate the field of view matched to the imaging field of the telescope. This provides a "stealth-like" imaging capability in the dark for battlefields and surveillance environments without revealing itself.

This multi-purpose Laser-Transceiver-Imager (LTI) provides a pulsed laser transceiver system that can be used for laser communications. In addition the lidar receiver detector can be a 2-dimensional array of avalanche photo-diodes (APD's) that allows 3-D imaging of the viewing scene. Each element in the array of APD devices can measure the range providing an array of range measurements within the field of regard.

All aspects of the system incorporate lightweight, compact and portable components. The laser is a fiber-based system that is lightweight and stable. The telescope is compact and lightweight for portability, which make it optimum for field use.

The fiber laser is optically excited by a single laser diode operating in a continuous wave configuration with a wavelength of, but not limited to, about 915 nm-980 nm. Approximately 35 µJ per pulse energy is extractable from the fiber laser. The single mode fiber operates in $TEM_{00}$ mode. An acousto-optic modulator introduces the controlled loss in the cavity for Q-switching. The fiber laser is capable of operating with several repetition frequencies, the minimum being 45 kHz and maximum 100 kHz. Each pulse emitted from the fiber laser has a width of 150 ns. The peak power of the fiber laser is 200 Watts with average power of 1.35 Watts. This corresponds to a range resolution of 22.5 meters, calculated using $D=c\tau/2$, in which "D" is distance to target, "c" is speed of light and "$\tau$" is pulse duration.

While the invention has been described with reference to specific embodiments, modifications and variations of the invention may be constructed without departing from the scope of the invention, which is defined in the following claims.

We claim:

1. A lightweight, compact, portable light detection and ranging system for measuring aerosols, clouds, and airborne pollution comprising a laser, a telescope coupled to the laser, optics coupled to the telescope and the laser, connectors coupling a coupler, a modulator and an amplifier to the laser, and a computing device for receiving and processing images from the laser and outputting data relative to processed images.

2. The system of claim 1, wherein the laser is a fiber laser.

3. The system of claim 2, wherein the fiber laser is an erbium-ytterbium co-doped fiber laser.

4. The system of claim 3, wherein the fiber laser operates at 1.55 µm.

5. The system of claim 3, further comprising at least one telescope communicating with the laser, wherein light emitted by the laser is collected by the at least one telescope.

6. The system of claim 5, further comprising a lightweight carbon-fiber tube housing for the telescope.

7. The system of claim 6, further comprising an afocal beam expander mounted in a lightweight carbon fiber tube comprising a lightweight primary mirror and a lightweight secondary mirror.

8. The system of claim 7, further comprising an interchangeable spider ring, wherein the secondary mirror is mounted on the interchangeable spider ring for providing a collimated input beam.

9. The system of claim 8, wherein the telescope operates in Cassegrain configuration, wherein the secondary mirror mounted on the interchangeable spider ring provides laser return in a Cassegrain focus.

10. The system of claim 9, wherein the telescope operates in dual light detection and ranging/imaging mode configuration.

11. The system of claim 10, further comprising a dichroic beam splitter, reimaging lens and an imaging camera and an imaging camera, wherein the secondary mirror mounted on the interchangeable spider ring provides return pulses through the dichroic beam splitter and re-imaging lens to the imaging camera.

12. The system of claim 11, wherein the dichroic beam splitter is disposed between a fiber-laser collimator and the telescope.

13. The system of claim 12, wherein the dichroic beam splitter reflects the laser beam towards the secondary mirror and allows light received by the telescope at visible wavelengths to pass through to the imaging camera aligned on a common optical axis with the beam splitter.

14. The system of claim 13, further comprising a laser interface for providing images for direct viewing, infrared scene illumination and stealth-viewing for surveillance.

15. The system of claim 14, wherein the system is a scanning aerosol detector.

16. The system of claim 15, wherein the detector provides information for measuring cloud height.

17. The system of claim 15, wherein the detector is a warning device to detect and warn of presence of ambient chemical and biological agents.

18. The system of claim 13, wherein the mirrors are of lightweight material.

19. The system of claim 18, wherein the material is borosilicate glass.

20. The system of claim 9, further comprising a re-imaging lens mounted in front of an imaging camera for providing a high magnification image.

21. The system of claim 5, wherein the telescope comprises an interchangeable spider ring for allowing variation of beam expansion ratios.

22. The system of claim 21, wherein the telescope further comprises at least one lightweight mirror.

23. The system of claim 22, wherein the mirror is of material having a ribbed or open cell structure.

24. The system of claim 23, wherein the mirror is made of glass heated in a kiln until it flows into a preformed machined cast with a ribbed structure containing open pockets, and is therefore lighter and stiffer than solid substrate mirrors.

25. The system of claim 22, wherein the telescope comprises lenses for receiving and transmitting laser emission from the laser.

26. The system of claim 25, wherein the telescope provides the laser emission through a plano-concave lens and a plano-convex lens to the mirror.

27. The system of claim 26, wherein the mirror comprises beam steering mirrors for aligning laser output pulses with the telescope tube.

28. The system of claim 27, wherein the mirrors comprise primary and secondary mirrors wherein the secondary mirror provides return laser pulses from the primary mirror through the lens.

29. The system of claim 27, further comprising a digital oscilloscope communicating with the computing device, the laser, the telescope and the amplifier.

30. The system of claim 29, further comprising a filter for filtering the laser pulses from the secondary mirror.

31. The system of claim 30, further comprising a two-dimensional array of avalanche photo-diodes for further light transmission.

32. The system of claim 31, further comprising a beam splitter for delivering a part of the laser emission to a detector as an input to the oscilloscope.

33. The system of claim 32, further comprising an imaging camera coupled to the beam splitter for transmitting light to the imaging camera.

34. The system of claim 2, wherein the numerical aperture of the fiber laser is 0.17.

35. A lightweight, compact, portable light detection and ranging system for measuring aerosols, clouds, and airborne pollution comprising a laser, a telescope coupled to the laser, optics coupled to the telescope and the laser, connectors for coupling a coupler, a modulator and an amplifier to the laser, and a computing device for receiving and processing images from the laser and outputting data relative to processed images, wherein the laser is a fiber ring laser comprising an erbium doped fiber amplifier.

36. The system of claim 35, wherein the optics comprise an optical isolator.

37. The system of claim 36, wherein the modulator is an acousto-optic modulator with a driver.

38. The system of claim 37, further comprising a pulse generator for controlling the modulator.

39. The system of claim 38, wherein the connectors are angled connections for coupling fibers of the fiber laser to the optical isolator, the acousto-optic modulator and the amplifier.

40. The system of claim 39, further comprising fiber splices and an output coupler, wherein the fiber splices connect the output coupler to the amplifier, modulator and the fiber laser.

41. A method for three-dimensional imaging of a viewing scene comprising imaging with a two-dimensional array of avalanche photo-diodes, providing a fiber laser operating in an eye-safe regime, receiving laser emission from the fiber laser, enhancing the emissions and transmitting with a transceiver, collecting 3-D cloud information or data of ambient aerosols, processing the information or data and outputting images or warnings about the processed information or data respectively.

42. The method of claim 41, wherein the providing the fiber laser comprises providing an erbium doped fiber laser.

43. The method of claim 42, wherein the providing the fiber laser comprises providing an erbium-ytterbium co-doped fiber laser.

44. The method of claim 41, wherein the receiving, enhancing and transmitting with a transceiver comprises receiving, enhancing and transmitting with an afocal telescope housed in a lightweight carbon fiber tube.

45. The method of claim 44, wherein the receiving comprises receiving a collimated input beam from the fiber laser and the enhancing comprises providing the input beam to a two-mirror afocal system and converting the input beam to a larger diameter collimated beam when leaving the telescope.

46. The method of claim 45, wherein the enhancing further comprises providing a primary mirror in the telescope, providing an interchangeable spider ring in the telescope and providing secondary mirrors on the ring.

47. The method of claim 46, wherein the enhancing comprises interchanging secondary mirrors on the ring and providing collimated beams having a different ranges of beam expansion ratios.

48. The method of claim 47, further comprising configuring the system in an imaging mode.

49. The method of claim 48, wherein the configuring in the imaging mode enables Cassegrain or Ritchey Chretien configurations.

50. The method of claim 48, wherein the configuring in the imaging mode enables afocal imaging configuration.

* * * * *